United States Patent
Ollerdessen

(10) Patent No.: US 7,684,842 B2
(45) Date of Patent: Mar. 23, 2010

(54) SYSTEM AND METHOD FOR PREVENTING SENSOR MISUSE

(75) Inventor: Albert L. Ollerdessen, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 343 days.

(21) Appl. No.: 11/541,251

(22) Filed: Sep. 29, 2006

(65) Prior Publication Data

US 2008/0081971 A1    Apr. 3, 2008

(51) Int. Cl.
*A61B 5/1455*    (2006.01)
(52) U.S. Cl. ...................... 600/323; 600/344
(58) Field of Classification Search ................. 600/323, 600/344
See application file for complete search history.

(56) References Cited

U.S. PATENT DOCUMENTS

| | | |
|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsey et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |

(Continued)

FOREIGN PATENT DOCUMENTS

DE    3405444    8/1985

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

(Continued)

*Primary Examiner*—Eric F Winakur
*Assistant Examiner*—Etsub D Berhanu
(74) *Attorney, Agent, or Firm*—Fletcher Yoder

(57) ABSTRACT

Embodiments of the present invention relate to a pulse oximetry sensor. The pulse oximetry sensor may comprise an emitter configured to transmit a signal into tissue, a detector configured to detect the signal, and a quality assurance component coupled to a first sensor component and second sensor component. The quality assurance component may be configured to break and disable the sensor upon separation of the first sensor component from the second sensor component.

21 Claims, 4 Drawing Sheets

U.S. PATENT DOCUMENTS

| | | |
|---|---|---|
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,039 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |

| Patent No. | Kind | Date | Inventor |
|---|---|---|---|
| 5,349,519 | A | 9/1994 | Kaestle |
| 5,349,952 | A | 9/1994 | McCarthy et al. |
| 5,349,953 | A | 9/1994 | McCarthy et al. |
| 5,351,685 | A | 10/1994 | Potratz |
| 5,353,799 | A | 10/1994 | Chance |
| 5,355,880 | A | 10/1994 | Thomas et al. |
| 5,355,882 | A | 10/1994 | Ukawa et al. |
| 5,361,758 | A | 11/1994 | Hall et al. |
| 5,365,066 | A | 11/1994 | Krueger, Jr. et al. |
| 5,368,025 | A | 11/1994 | Young et al. |
| 5,368,026 | A | 11/1994 | Swedlow et al. |
| 5,368,224 | A | 11/1994 | Richardson et al. |
| 5,372,136 | A | 12/1994 | Steuer et al. |
| 5,377,675 | A | 1/1995 | Ruskewicz et al. |
| 5,385,143 | A | 1/1995 | Aoyagi |
| 5,387,122 | A | 2/1995 | Goldberger et al. |
| 5,390,670 | A | 2/1995 | Centa et al. |
| 5,392,777 | A | 2/1995 | Swedlow et al. |
| 5,398,680 | A | 3/1995 | Polson et al. |
| 5,402,777 | A | 4/1995 | Warring et al. |
| 5,402,779 | A | 4/1995 | Chen et al. |
| 5,411,023 | A | 5/1995 | Morris, Sr. et al. |
| 5,411,024 | A | 5/1995 | Thomas et al. |
| 5,413,099 | A | 5/1995 | Schmidt et al. |
| 5,413,100 | A | 5/1995 | Barthelemy et al. |
| 5,413,101 | A | 5/1995 | Sugiura |
| 5,413,102 | A | 5/1995 | Schmidt et al. |
| 5,417,207 | A | 5/1995 | Young et al. |
| 5,421,329 | A | 6/1995 | Casciani et al. |
| 5,425,360 | A | 6/1995 | Nelson |
| 5,425,362 | A | 6/1995 | Siker et al. |
| 5,427,093 | A | 6/1995 | Ogawa et al. |
| 5,429,128 | A | 7/1995 | Cadell et al. |
| 5,429,129 | A | 7/1995 | Lovejoy et al. |
| 5,431,159 | A | 7/1995 | Baker et al. |
| 5,431,170 | A | 7/1995 | Mathews |
| 5,437,275 | A | 8/1995 | Amundsen et al. |
| 5,438,986 | A | 8/1995 | Disch et al. |
| 5,448,991 | A | 9/1995 | Polson et al. |
| 5,452,717 | A | 9/1995 | Branigan et al. |
| 5,465,714 | A | 11/1995 | Scheuing |
| 5,469,845 | A | 11/1995 | DeLonzor et al. |
| RE35,122 | E | 12/1995 | Corenman et al. |
| 5,482,034 | A | 1/1996 | Lewis et al. |
| 5,482,036 | A | 1/1996 | Diab et al. |
| 5,485,847 | A | 1/1996 | Baker, Jr. |
| 5,490,505 | A | 2/1996 | Diab et al. |
| 5,490,523 | A | 2/1996 | Isaacson et al. |
| 5,491,299 | A | 2/1996 | Naylor et al. |
| 5,494,032 | A | 2/1996 | Robinson et al. |
| 5,494,043 | A | 2/1996 | O'Sullivan et al. |
| 5,497,771 | A | 3/1996 | Rosenheimer |
| 5,499,627 | A | 3/1996 | Steuer et al. |
| 5,503,148 | A | 4/1996 | Pologe et al. |
| 5,505,199 | A | 4/1996 | Kim |
| 5,507,286 | A | 4/1996 | Solenberger |
| 5,511,546 | A | 4/1996 | Hon |
| 5,517,988 | A | 5/1996 | Gerhard |
| 5,520,177 | A | 5/1996 | Ogawa et al. |
| 5,521,851 | A | 5/1996 | Wei et al. |
| 5,522,388 | A | 6/1996 | Ishikawa et al. |
| 5,524,617 | A | 6/1996 | Mannheimer |
| 5,529,064 | A | 6/1996 | Rall et al. |
| 5,533,507 | A | 7/1996 | Potratz et al. |
| 5,551,423 | A | 9/1996 | Sugiura |
| 5,551,424 | A | 9/1996 | Morrison et al. |
| 5,553,614 | A | 9/1996 | Chance |
| 5,553,615 | A | 9/1996 | Carim et al. |
| 5,555,882 | A | 9/1996 | Richardson et al. |
| 5,558,096 | A | 9/1996 | Palatnik |
| 5,560,355 | A | 10/1996 | Merchant et al. |
| 5,564,417 | A | 10/1996 | Chance |
| 5,575,284 | A | 11/1996 | Athan et al. |
| 5,575,285 | A | 11/1996 | Takanashi et al. |
| 5,577,500 | A | 11/1996 | Potratz |
| 5,582,169 | A | 12/1996 | Oda et al. |
| 5,584,296 | A | 12/1996 | Cui et al. |
| 5,588,425 | A | 12/1996 | Sackner et al. |
| 5,588,427 | A | 12/1996 | Tien |
| 5,590,652 | A | 1/1997 | Inai |
| 5,595,176 | A | 1/1997 | Yamaura |
| 5,596,986 | A | 1/1997 | Goldfarb |
| 5,611,337 | A | 3/1997 | Bukta |
| 5,617,852 | A | 4/1997 | MacGregor |
| 5,619,992 | A | 4/1997 | Guthrie et al. |
| 5,626,140 | A | 5/1997 | Feldman et al. |
| 5,630,413 | A | 5/1997 | Thomas et al. |
| 5,632,272 | A | 5/1997 | Diab et al. |
| 5,632,273 | A | 5/1997 | Suzuki |
| 5,634,459 | A | 6/1997 | Gardosi |
| 5,638,593 | A | 6/1997 | Gerhardt et al. |
| 5,638,816 | A | 6/1997 | Kiani-Azarbayjany et al. |
| 5,638,818 | A | 6/1997 | Diab et al. |
| 5,645,060 | A | 7/1997 | Yorkey et al. |
| 5,645,440 | A | 7/1997 | Tobler et al. |
| 5,660,567 | A | 8/1997 | Nierlich et al. |
| 5,662,105 | A | 9/1997 | Tien |
| 5,662,106 | A | 9/1997 | Swedlow et al. |
| 5,664,270 | A | 9/1997 | Bell et al. |
| 5,666,952 | A | 9/1997 | Fuse et al. |
| 5,671,529 | A | 9/1997 | Nelson |
| 5,673,692 | A | 10/1997 | Schulze et al. |
| 5,673,693 | A | 10/1997 | Solenberger |
| 5,676,139 | A | 10/1997 | Goldberger et al. |
| 5,676,141 | A | 10/1997 | Hollub |
| 5,678,544 | A | 10/1997 | DeLonzor et al. |
| 5,680,857 | A | 10/1997 | Pelikan et al. |
| 5,685,299 | A | 11/1997 | Diab et al. |
| 5,685,301 | A | 11/1997 | Klomhaus |
| 5,687,719 | A | 11/1997 | Sato et al. |
| 5,687,722 | A | 11/1997 | Tien et al. |
| 5,692,503 | A | 12/1997 | Kuenstner |
| 5,692,505 | A | 12/1997 | Fouts |
| 5,709,205 | A | 1/1998 | Bukta |
| 5,713,355 | A | 2/1998 | Richardson et al. |
| 5,724,967 | A | 3/1998 | Venkatachalam |
| 5,727,547 | A | 3/1998 | Levinson et al. |
| 5,730,124 | A | 3/1998 | Yamauchi |
| 5,731,582 | A | 3/1998 | West |
| D393,830 | S | 4/1998 | Tobler et al. |
| 5,743,260 | A | 4/1998 | Chung et al. |
| 5,743,262 | A | 4/1998 | Lepper, Jr. et al. |
| 5,743,263 | A | 4/1998 | Baker, Jr. |
| 5,746,206 | A | 5/1998 | Mannheimer |
| 5,746,697 | A | 5/1998 | Swedlow et al. |
| 5,752,914 | A | 5/1998 | DeLonzor et al. |
| 5,755,226 | A | 5/1998 | Carim et al. |
| 5,758,644 | A | 6/1998 | Diab et al. |
| 5,760,910 | A | 6/1998 | Lepper, Jr. et al. |
| 5,766,125 | A | 6/1998 | Aoyagi et al. |
| 5,766,127 | A | 6/1998 | Pologe et al. |
| 5,769,785 | A | 6/1998 | Diab et al. |
| 5,772,587 | A | 6/1998 | Gratton et al. |
| 5,774,213 | A | 6/1998 | Trebino et al. |
| 5,776,058 | A | 7/1998 | Levinson et al. |
| 5,776,059 | A | 7/1998 | Kaestle |
| 5,779,630 | A | 7/1998 | Fein et al. |
| 5,779,631 | A | 7/1998 | Chance |
| 5,782,237 | A | 7/1998 | Casciani et al. |
| 5,782,756 | A | 7/1998 | Mannheimer |
| 5,782,757 | A | 7/1998 | Diab et al. |
| 5,782,758 | A | 7/1998 | Ausec et al. |
| 5,786,592 | A | 7/1998 | Hök |
| 5,788,634 | A | 8/1998 | Suda et al. |
| 5,790,729 | A | 8/1998 | Pologe et al. |
| 5,792,052 | A | 8/1998 | Isaacson et al. |

| | | | | | | |
|---|---|---|---|---|---|---|
| 5,795,292 | A | 8/1998 | Lewis et al. | 5,987,343 A | 11/1999 | Kinast |
| 5,797,841 | A | 8/1998 | DeLonzor et al. | 5,991,648 A | 11/1999 | Levin |
| 5,800,348 | A | 9/1998 | Kaestle | 5,995,855 A | 11/1999 | Kiani et al. |
| 5,800,349 | A | 9/1998 | Isaacson et al. | 5,995,856 A | 11/1999 | Mannheimer et al. |
| 5,803,910 | A | 9/1998 | Potratz | 5,995,858 A | 11/1999 | Kinast |
| 5,807,246 | A | 9/1998 | Sakaguchi et al. | 5,995,859 A | 11/1999 | Takahashi |
| 5,807,247 | A | 9/1998 | Merchant et al. | 5,997,343 A | 12/1999 | Mills et al. |
| 5,807,248 | A | 9/1998 | Mills | 5,999,834 A | 12/1999 | Wang et al. |
| 5,810,723 | A | 9/1998 | Aldrich | 6,002,952 A | 12/1999 | Diab et al. |
| 5,810,724 | A | 9/1998 | Gronvall | 6,005,658 A | 12/1999 | Kaluza et al. |
| 5,813,980 | A | 9/1998 | Levinson et al. | 6,006,120 A | 12/1999 | Levin |
| 5,817,008 | A | 10/1998 | Rafert et al. | 6,011,985 A | 1/2000 | Athan et al. |
| 5,817,009 | A | 10/1998 | Rosenheimer et al. | 6,011,986 A | 1/2000 | Diab et al. |
| 5,817,010 | A | 10/1998 | Hibl | 6,014,576 A | 1/2000 | Raley et al. |
| 5,818,985 | A | 10/1998 | Merchant et al. | 6,018,673 A | 1/2000 | Chin et al. |
| 5,820,550 | A | 10/1998 | Polson et al. | 6,018,674 A | 1/2000 | Aronow |
| 5,823,950 | A | 10/1998 | Diab et al. | 6,022,321 A | 2/2000 | Amano et al. |
| 5,823,952 | A | 10/1998 | Levinson et al. | 6,023,541 A | 2/2000 | Merchant et al. |
| 5,827,179 | A | 10/1998 | Lichter et al. | 6,026,312 A | 2/2000 | Shemwell et al. |
| 5,827,182 | A | 10/1998 | Raley et al. | 6,026,314 A | 2/2000 | Amerov et al. |
| 5,829,439 | A | 11/1998 | Yokosawa et al. | 6,031,603 A | 2/2000 | Fine et al. |
| 5,830,135 | A | 11/1998 | Bosque et al. | 6,035,223 A | 3/2000 | Baker, Jr. |
| 5,830,136 | A | 11/1998 | DeLonzor et al. | 6,036,642 A | 3/2000 | Diab et al. |
| 5,830,137 | A | 11/1998 | Scharf | 6,041,247 A | 3/2000 | Weckstrom et al. |
| 5,839,439 | A | 11/1998 | Nierlich et al. | 6,044,283 A | 3/2000 | Fein et al. |
| RE36,000 | E | 12/1998 | Swedlow et al. | 6,047,201 A | 4/2000 | Jackson, III |
| 5,842,979 | A | 12/1998 | Jarman et al. | 6,055,447 A | 4/2000 | Weil |
| 5,842,981 | A | 12/1998 | Larsen et al. | 6,061,584 A | 5/2000 | Lovejoy et al. |
| 5,842,982 | A | 12/1998 | Mannheimer | 6,064,898 A | 5/2000 | Aldrich |
| 5,846,190 | A | 12/1998 | Woehrle | 6,064,899 A | 5/2000 | Fein et al. |
| 5,851,178 | A | 12/1998 | Aronow | 6,067,462 A | 5/2000 | Diab et al. |
| 5,851,179 | A | 12/1998 | Ritson et al. | 6,073,038 A | 6/2000 | Wang et al. |
| 5,853,364 | A | 12/1998 | Baker, Jr. et al. | 6,078,829 A | 6/2000 | Uchida |
| 5,860,919 | A | 1/1999 | Kiani-Azarbayjany et al. | 6,078,833 A | 6/2000 | Hueber |
| 5,865,736 | A | 2/1999 | Baker, Jr. et al. | 6,081,735 A | 6/2000 | Diab et al. |
| 5,879,294 | A | 3/1999 | Anderson et al. | 6,083,157 A | 7/2000 | Noller |
| 5,885,213 | A | 3/1999 | Richardson et al. | 6,083,172 A | 7/2000 | Baker, Jr. et al. |
| 5,890,929 | A | 4/1999 | Mills et al. | 6,088,607 A | 7/2000 | Diab et al. |
| 5,891,021 | A | 4/1999 | Dillon et al. | 6,094,592 A | 7/2000 | Yorkey et al. |
| 5,891,022 | A | 4/1999 | Pologe | 6,095,974 A | 8/2000 | Shemwell et al. |
| 5,891,024 | A | 4/1999 | Jarman et al. | 6,104,938 A | 8/2000 | Huiku et al. |
| 5,891,025 | A | 4/1999 | Buschmann et al. | 6,104,939 A | 8/2000 | Groner |
| 5,891,026 | A | 4/1999 | Wang et al. | 6,112,107 A | 8/2000 | Hannula |
| 5,902,235 | A | 5/1999 | Lewis et al. | 6,113,541 A | 9/2000 | Dias et al. |
| 5,910,108 | A | 6/1999 | Solenberger | 6,115,621 A | 9/2000 | Chin |
| 5,911,690 | A | 6/1999 | Rall | 6,122,535 A | 9/2000 | Kaestle et al. |
| 5,912,656 | A | 6/1999 | Tham et al. | 6,133,994 A | 10/2000 | Mathews et al. |
| 5,913,819 | A | 6/1999 | Taylor et al. | 6,135,952 A | 10/2000 | Coetzee |
| 5,916,154 | A | 6/1999 | Hobbs et al. | 6,144,444 A | 11/2000 | Haworth et al. |
| 5,916,155 | A | 6/1999 | Levinson et al. | 6,144,867 A | 11/2000 | Walker et al. |
| 5,919,133 | A | 7/1999 | Taylor et al. | 6,144,868 A | 11/2000 | Parker |
| 5,919,134 | A | 7/1999 | Diab | 6,149,481 A | 11/2000 | Wang et al. |
| 5,920,263 | A | 7/1999 | Huttenhoff et al. | 6,151,107 A | 11/2000 | Schöllermann et al. |
| 5,921,921 | A | 7/1999 | Potratz et al. | 6,151,516 A | 11/2000 | Kiani-Azarbayjani et al. |
| 5,922,607 | A | 7/1999 | Bernreuter | 6,151,518 A | 11/2000 | Hayashi |
| 5,924,979 | A | 7/1999 | Swedlow et al. | 6,152,754 A | 11/2000 | Gerhardt et al. |
| 5,924,980 | A | 7/1999 | Coetzee | 6,154,667 A | 11/2000 | Miura et al. |
| 5,924,982 | A | 7/1999 | Chin | 6,157,850 A | 12/2000 | Diab et al. |
| 5,924,985 | A | 7/1999 | Jones | 6,159,147 A | 12/2000 | Lichter |
| 5,934,277 | A | 8/1999 | Mortz | 6,163,715 A | 12/2000 | Larsen et al. |
| 5,934,925 | A | 8/1999 | Tobler et al. | 6,165,005 A | 12/2000 | Mills et al. |
| 5,940,182 | A | 8/1999 | Lepper, Jr. et al. | 6,173,196 B1 | 1/2001 | Delonzor et al. |
| 5,954,644 | A | 9/1999 | Dettling et al. | 6,178,343 B1 | 1/2001 | Bindszus et al. |
| 5,957,840 | A | 9/1999 | Terasawa et al. | 6,179,159 B1 | 1/2001 | Gurley |
| 5,960,610 | A | 10/1999 | Levinson et al. | 6,181,958 B1 | 1/2001 | Steuer et al. |
| 5,961,450 | A | 10/1999 | Merchant et al. | 6,181,959 B1 | 1/2001 | Schöllermann et al. |
| 5,961,452 | A | 10/1999 | Chung et al. | 6,184,521 B1 | 2/2001 | Coffin, IV et al. |
| 5,964,701 | A | 10/1999 | Asada et al. | 6,188,470 B1 | 2/2001 | Grace |
| 5,971,930 | A | 10/1999 | Elghazzawi | 6,192,260 B1 | 2/2001 | Chance |
| 5,978,691 | A | 11/1999 | Mills | 6,195,575 B1 | 2/2001 | Levinson |
| 5,978,693 | A | 11/1999 | Hamilton et al. | 6,198,951 B1 | 3/2001 | Kosuda et al. |
| 5,983,120 | A | 11/1999 | Groner et al. | 6,206,830 B1 | 3/2001 | Diab et al. |
| 5,983,122 | A | 11/1999 | Jarman et al. | 6,213,952 B1 | 4/2001 | Finarov et al. |

| | | | | | | |
|---|---|---|---|---|---|---|
| 6,217,523 | B1 | 4/2001 | Amano et al. | 6,438,396 | B1 | 8/2002 | Cook |
| 6,222,189 | B1 | 4/2001 | Misner et al. | 6,438,399 | B1 | 8/2002 | Kurth |
| 6,223,064 | B1 | 4/2001 | Lynn | 6,449,501 | B1 | 9/2002 | Reuss |
| 6,226,539 | B1 | 5/2001 | Potratz | 6,453,183 | B1 | 9/2002 | Walker |
| 6,226,540 | B1 | 5/2001 | Bernreuter et al. | 6,453,184 | B1 | 9/2002 | Hyogo et al. |
| 6,229,856 | B1 | 5/2001 | Diab et al. | 6,456,862 | B2 | 9/2002 | Benni |
| 6,230,035 | B1 | 5/2001 | Aoyagi et al. | 6,461,305 | B1 | 10/2002 | Schnall |
| 6,233,470 | B1 | 5/2001 | Tsuchiya | 6,463,310 | B1 | 10/2002 | Swedlow et al. |
| 6,236,871 | B1 | 5/2001 | Tsuchiya | 6,463,311 | B1 | 10/2002 | Diab |
| 6,236,872 | B1 | 5/2001 | Diab et al. | 6,466,808 | B1 | 10/2002 | Chin et al. |
| 6,240,305 | B1 | 5/2001 | Tsuchiya | 6,466,809 | B1 | 10/2002 | Riley |
| 6,253,097 | B1 | 6/2001 | Aronow et al. | 6,470,199 | B1 | 10/2002 | Kopotic et al. |
| 6,253,098 | B1 | 6/2001 | Walker et al. | 6,470,200 | B2 | 10/2002 | Walker et al. |
| 6,256,523 | B1 | 7/2001 | Diab et al. | 6,480,729 | B2 | 11/2002 | Stone |
| 6,256,524 | B1 | 7/2001 | Walker et al. | 6,490,466 | B1 | 12/2002 | Fein et al. |
| 6,261,236 | B1 | 7/2001 | Grimblatov | 6,493,568 | B1 | 12/2002 | Bell |
| 6,263,221 | B1 | 7/2001 | Chance et al. | 6,496,711 | B1 | 12/2002 | Athan et al. |
| 6,263,222 | B1 | 7/2001 | Diab et al. | 6,498,942 | B1 | 12/2002 | Esenaliev et al. |
| 6,263,223 | B1 | 7/2001 | Shepherd et al. | 6,501,974 | B2 | 12/2002 | Huiku |
| 6,266,546 | B1 | 7/2001 | Steuer et al. | 6,501,975 | B2 | 12/2002 | Diab et al. |
| 6,266,547 | B1 | 7/2001 | Walker et al. | 6,505,060 | B1 | 1/2003 | Norris |
| 6,272,363 | B1 | 8/2001 | Casciani et al. | 6,505,061 | B2 | 1/2003 | Larson |
| 6,278,522 | B1 | 8/2001 | Lepper, Jr. et al. | 6,505,133 | B1 | 1/2003 | Hanna et al. |
| 6,280,213 | B1 | 8/2001 | Tobler et al. | 6,510,329 | B2 | 1/2003 | Heckel |
| 6,280,381 | B1 | 8/2001 | Malin et al. | 6,510,331 | B1 | 1/2003 | Williams et al. |
| 6,285,894 | B1 | 9/2001 | Oppelt et al. | 6,512,937 | B2 | 1/2003 | Blank et al. |
| 6,285,895 | B1 | 9/2001 | Ristolainen et al. | 6,515,273 | B2 | 2/2003 | Al-Ali |
| 6,285,896 | B1 | 9/2001 | Tobler et al. | 6,519,484 | B1 | 2/2003 | Lovejoy et al. |
| 6,298,252 | B1 | 10/2001 | Kovach et al. | 6,519,486 | B1 | 2/2003 | Edgar, Jr. et al. |
| 6,308,089 | B1 | 10/2001 | Von der Ruhr et al. | 6,519,487 | B1 | 2/2003 | Parker |
| 6,321,100 | B1 | 11/2001 | Parker | 6,525,386 | B1 | 2/2003 | Mills et al. |
| 6,330,468 | B1 | 12/2001 | Scharf | 6,526,300 | B1 | 2/2003 | Kiani et al. |
| 6,334,065 | B1 | 12/2001 | Al-Ali et al. | 6,526,301 | B2 | 2/2003 | Larsen et al. |
| 6,339,715 | B1 | 1/2002 | Bahr et al. | 6,541,756 | B2 | 4/2003 | Schulz et al. |
| 6,342,039 | B1 | 1/2002 | Lynn | 6,542,764 | B1 | 4/2003 | Al-Ali et al. |
| 6,343,223 | B1 | 1/2002 | Chin et al. | 6,546,267 | B1 | 4/2003 | Sugiura et al. |
| 6,343,224 | B1 | 1/2002 | Parker | 6,553,241 | B2 | 4/2003 | Mannheimer et al. |
| 6,349,228 | B1 | 2/2002 | Kiani et al. | 6,553,242 | B1 | 4/2003 | Sarussi |
| 6,351,658 | B1 | 2/2002 | Middleman et al. | 6,553,243 | B2 | 4/2003 | Gurley |
| 6,353,750 | B1 | 3/2002 | Kimura | 6,554,788 | B1 | 4/2003 | Hunley |
| 6,356,774 | B1 | 3/2002 | Bernstein et al. | 6,556,852 | B1 | 4/2003 | Schulze et al. |
| 6,360,113 | B1 | 3/2002 | Dettling | 6,560,470 | B1 | 5/2003 | Pologe |
| 6,360,114 | B1 | 3/2002 | Diab et al. | 6,564,077 | B2 | 5/2003 | Mortara |
| 6,361,501 | B1 | 3/2002 | Amano et al. | 6,564,088 | B1 | 5/2003 | Soller et al. |
| 6,363,269 | B1 | 3/2002 | Hanna et al. | 6,571,113 | B1 | 5/2003 | Fein et al. |
| D455,834 | S | 4/2002 | Donars et al. | 6,571,114 | B1 | 5/2003 | Koike et al. |
| 6,370,408 | B1 | 4/2002 | Merchant et al. | 6,574,491 | B2 | 6/2003 | Elghazzawi |
| 6,370,409 | B1 | 4/2002 | Chung et al. | 6,580,086 | B1 | 6/2003 | Schulz et al. |
| 6,371,921 | B1 | 4/2002 | Caro | 6,584,336 | B1 | 6/2003 | Ali et al. |
| 6,374,129 | B1 | 4/2002 | Chin et al. | 6,587,703 | B2 | 7/2003 | Cheng et al. |
| 6,377,829 | B1 | 4/2002 | Al-Ali et al. | 6,587,704 | B1 | 7/2003 | Fine et al. |
| 6,381,479 | B1 | 4/2002 | Norris | 6,589,172 | B2 | 7/2003 | Williams et al. |
| 6,381,480 | B1 | 4/2002 | Stoddar et al. | 6,591,122 | B2 | 7/2003 | Schmitt |
| 6,385,471 | B1 | 5/2002 | Mortz | 6,591,123 | B2 | 7/2003 | Fein et al. |
| 6,385,821 | B1 | 5/2002 | Modgil et al. | 6,594,511 | B2 | 7/2003 | Stone et al. |
| 6,388,240 | B2 | 5/2002 | Schulz et al. | 6,594,512 | B2 | 7/2003 | Huang |
| 6,393,310 | B1 | 5/2002 | Kuenster | 6,594,513 | B1 | 7/2003 | Jobsis et al. |
| 6,393,311 | B1 | 5/2002 | Edgar, Jr. et al. | 6,597,931 | B1 | 7/2003 | Cheng et al. |
| 6,397,091 | B2 | 5/2002 | Diab et al. | 6,597,933 | B2 | 7/2003 | Kiani et al. |
| 6,397,092 | B1 | 5/2002 | Norris et al. | 6,600,940 | B1 | 7/2003 | Fein et al. |
| 6,397,093 | B1 | 5/2002 | Aldrich | 6,606,510 | B2 | 8/2003 | Swedlow et al. |
| 6,400,971 | B1 | 6/2002 | Finarov et al. | 6,606,511 | B1 | 8/2003 | Ali et al. |
| 6,400,972 | B1 | 6/2002 | Fine | 6,606,512 | B2 | 8/2003 | Muz et al. |
| 6,400,973 | B1 | 6/2002 | Winter | 6,608,562 | B1 | 8/2003 | Kimura et al. |
| 6,402,690 | B1 | 6/2002 | Rhee et al. | 6,609,016 | B1 | 8/2003 | Lynn |
| 6,408,198 | B1 | 6/2002 | Hanna et al. | 6,615,064 | B1 | 9/2003 | Aldrich |
| 6,411,832 | B1 | 6/2002 | Guthermann | 6,615,065 | B1 | 9/2003 | Barrett et al. |
| 6,411,833 | B1 | 6/2002 | Baker, Jr. et al. | 6,618,602 | B2 | 9/2003 | Levin et al. |
| 6,421,549 | B1 | 7/2002 | Jacques | 6,622,034 | B1 | 9/2003 | Gorski et al. |
| 6,430,423 | B2 | 8/2002 | DeLonzor et al. | 6,628,975 | B1 | 9/2003 | Fein et al. |
| 6,430,513 | B1 | 8/2002 | Wang et al. | 6,631,281 | B1 | 10/2003 | Kästle |
| 6,430,525 | B1 | 8/2002 | Weber et al. | 6,632,181 | B2 | 10/2003 | Flaherty |
| 6,434,408 | B1 | 8/2002 | Heckel et al. | 6,640,116 | B2 | 10/2003 | Diab |

| | | |
|---|---|---|
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,963,767 B2 | 11/2005 | Rantala et al. |
| 6,968,221 B2 | 11/2005 | Rosenthal |
| 6,971,580 B2 | 12/2005 | DeLonzor et al. |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boaz et al. |

| | | | | | | |
|---|---|---|---|---|---|---|
| 7,060,035 B2 | 6/2006 | Wasserman et al. | | 2004/0006261 A1 | 1/2004 | Swedlow et al. |
| 7,062,307 B2 | 6/2006 | Norris et al. | | 2004/0010188 A1 | 1/2004 | Wasserman et al. |
| 7,067,893 B2 | 6/2006 | Mills et al. | | 2004/0024297 A1 | 2/2004 | Chen et al. |
| 7,072,701 B2 | 7/2006 | Chen et al. | | 2004/0024326 A1 | 2/2004 | Yeo et al. |
| 7,072,702 B2 | 7/2006 | Edgar, Jr. et al. | | 2004/0034293 A1 | 2/2004 | Kimball |
| 7,079,880 B2 | 7/2006 | Stetson | | 2004/0039272 A1 | 2/2004 | Abdul-Hafiz et al. |
| 7,085,597 B2 | 8/2006 | Fein et al. | | 2004/0039273 A1 | 2/2004 | Terry |
| 7,096,052 B2 | 8/2006 | Mason et al. | | 2004/0054269 A1 | 3/2004 | Rantala et al. |
| 7,096,054 B2 | 8/2006 | Abdul-Hafiz et al. | | 2004/0054291 A1 | 3/2004 | Schulz et al. |
| 7,107,088 B2 | 9/2006 | Aceti | | 2004/0059209 A1 | 3/2004 | Al-Ali et al. |
| 7,113,815 B2 | 9/2006 | O'Neil et al. | | 2004/0059210 A1 | 3/2004 | Stetson |
| 7,123,950 B2 | 10/2006 | Mannheimer | | 2004/0064020 A1 | 4/2004 | Diab et al. |
| 7,127,278 B2 | 10/2006 | Melker et al. | | 2004/0068164 A1 | 4/2004 | Diab et al. |
| 7,130,671 B2 | 10/2006 | Baker, Jr. et al. | | 2004/0087846 A1 | 5/2004 | Wasserman |
| 7,132,641 B2 | 11/2006 | Schulz et al. | | 2004/0092805 A1 | 5/2004 | Yarita |
| 7,133,711 B2 | 11/2006 | Chernoguz et al. | | 2004/0097797 A1 | 5/2004 | Porges et al. |
| 7,139,559 B2 | 11/2006 | Terry | | 2004/0098009 A1 | 5/2004 | Boecker et al. |
| 7,142,901 B2 | 11/2006 | Kiani et al. | | 2004/0107065 A1 | 6/2004 | Al-Ali et al. |
| 7,162,288 B2 | 1/2007 | Nordstrom | | 2004/0116788 A1 | 6/2004 | Chernoguz et al. |
| 7,190,987 B2 | 3/2007 | Lindekugel et al. | | 2004/0116789 A1 | 6/2004 | Boaz et al. |
| 7,198,778 B2 | 4/2007 | Mannheimer et al. | | 2004/0117891 A1 | 6/2004 | Hannula et al. |
| 7,215,984 B2 | 5/2007 | Diab et al. | | 2004/0122300 A1 | 6/2004 | Boas et al. |
| 7,225,006 B2 | 5/2007 | Al-Ali et al. | | 2004/0122302 A1 | 6/2004 | Mason et al. |
| 7,225,007 B2 | 5/2007 | Al-Ali et al. | | 2004/0133087 A1 | 7/2004 | Ali et al. |
| 7,228,161 B2 | 6/2007 | Chin | | 2004/0133088 A1 | 7/2004 | Al-Ali et al. |
| 7,236,881 B2 | 6/2007 | Schmitt et al. | | 2004/0138538 A1 | 7/2004 | Stetson |
| 7,248,910 B2 | 7/2007 | Li et al. | | 2004/0138540 A1 | 7/2004 | Baker, Jr. et al. |
| 7,254,433 B2 | 8/2007 | Diab et al. | | 2004/0143172 A1 | 7/2004 | Fudge et al. |
| 7,254,434 B2 | 8/2007 | Schulz et al. | | 2004/0147821 A1 | 7/2004 | Al-Ali et al. |
| 7,272,425 B2 | 9/2007 | Al-Ali | | 2004/0147822 A1 | 7/2004 | Al-Ali et al. |
| 7,280,858 B2 | 10/2007 | Al-Ali et al. | | 2004/0147823 A1 | 7/2004 | Kiani et al. |
| 7,295,866 B2 | 11/2007 | Al-Ali et al. | | 2004/0147824 A1 | 7/2004 | Diab et al. |
| 7,305,262 B2 | 12/2007 | Brodnick et al. | | 2004/0152965 A1 | 8/2004 | Diab et al. |
| 7,315,753 B2 | 1/2008 | Baker, Jr. et al. | | 2004/0158134 A1 | 8/2004 | Diab et al. |
| 7,440,788 B2 | 10/2008 | Jenkins et al. | | 2004/0158135 A1 | 8/2004 | Baker, Jr. et al. |
| 2001/0021803 A1 | 9/2001 | Blank et al. | | 2004/0162472 A1 | 8/2004 | Berson et al. |
| 2001/0051767 A1 | 12/2001 | Williams et al. | | 2004/0167381 A1 | 8/2004 | Lichter |
| 2002/0016537 A1 | 2/2002 | Muz et al. | | 2004/0171920 A1 | 9/2004 | Mannheimer et al. |
| 2002/0026109 A1 | 2/2002 | Diab et al. | | 2004/0171948 A1 | 9/2004 | Terry |
| 2002/0028990 A1 | 3/2002 | Sheperd et al. | | 2004/0176671 A1 | 9/2004 | Fine et al. |
| 2002/0038078 A1 | 3/2002 | Ito | | 2004/0181133 A1 | 9/2004 | Al-Ali et al. |
| 2002/0042558 A1 | 4/2002 | Mendelson | | 2004/0181134 A1 | 9/2004 | Baker, Jr. et al. |
| 2002/0068859 A1 | 6/2002 | Knopp | | 2004/0186358 A1 | 9/2004 | Chernow et al. |
| 2002/0072681 A1 | 6/2002 | Schnall | | 2004/0199063 A1 | 10/2004 | O'Neil et al. |
| 2002/0115919 A1* | 8/2002 | Al-Ali ........................ 600/323 | | 2004/0204636 A1 | 10/2004 | Diab et al. |
| 2002/0116797 A1 | 8/2002 | Modgil et al. | | 2004/0204637 A1 | 10/2004 | Diab et al. |
| 2002/0128544 A1 | 9/2002 | Diab et al. | | 2004/0204638 A1 | 10/2004 | Diab et al. |
| 2002/0133067 A1 | 9/2002 | Jackson, III | | 2004/0204639 A1 | 10/2004 | Casciani et al. |
| 2002/0156354 A1 | 10/2002 | Larson | | 2004/0204865 A1 | 10/2004 | Lee et al. |
| 2002/0173706 A1 | 11/2002 | Takatani | | 2004/0210146 A1 | 10/2004 | Diab et al. |
| 2002/0173709 A1 | 11/2002 | Fine et al. | | 2004/0215069 A1 | 10/2004 | Mannheimer |
| 2002/0190863 A1 | 12/2002 | Lynn | | 2004/0215085 A1 | 10/2004 | Schnall |
| 2002/0198442 A1 | 12/2002 | Rantala et al. | | 2004/0230107 A1 | 11/2004 | Asada et al. |
| 2003/0018243 A1 | 1/2003 | Gerhardt et al. | | 2004/0230108 A1 | 11/2004 | Melker et al. |
| 2003/0036690 A1 | 2/2003 | Geddes et al. | | 2004/0236196 A1 | 11/2004 | Diab et al. |
| 2003/0045785 A1 | 3/2003 | Diab et al. | | 2004/0242980 A1 | 12/2004 | Kiani et al. |
| 2003/0073889 A1 | 4/2003 | Keilbach et al. | | 2004/0249252 A1 | 12/2004 | Fine et al. |
| 2003/0073890 A1 | 4/2003 | Hanna | | 2004/0257557 A1 | 12/2004 | Block et al. |
| 2003/0100840 A1 | 5/2003 | Sugiura et al. | | 2004/0260161 A1 | 12/2004 | Melker et al. |
| 2003/0132495 A1 | 7/2003 | Mills et al. | | 2004/0267103 A1 | 12/2004 | Li et al. |
| 2003/0135099 A1 | 7/2003 | Al-Ali | | 2004/0267104 A1 | 12/2004 | Hannula et al. |
| 2003/0162414 A1 | 8/2003 | Schulz et al. | | 2004/0267140 A1 | 12/2004 | Ito et al. |
| 2003/0171662 A1 | 9/2003 | O'Connor et al. | | 2005/0004479 A1 | 1/2005 | Townsend et al. |
| 2003/0176776 A1 | 9/2003 | Huiku | | 2005/0010092 A1 | 1/2005 | Weber et al. |
| 2003/0181799 A1 | 9/2003 | Lindekugel et al. | | 2005/0014999 A1 | 1/2005 | Rahe-Meyer |
| 2003/0187337 A1 | 10/2003 | Tarassenko et al. | | 2005/0020887 A1 | 1/2005 | Goldberg |
| 2003/0195402 A1 | 10/2003 | Fein et al. | | 2005/0020894 A1 | 1/2005 | Norris et al. |
| 2003/0197679 A1 | 10/2003 | Ali et al. | | 2005/0033128 A1 | 2/2005 | Ali et al. |
| 2003/0212316 A1 | 11/2003 | Leiden et al. | | 2005/0033129 A1 | 2/2005 | Edgar, Jr. et al. |
| 2003/0225323 A1 | 12/2003 | Kiani et al. | | 2005/0033131 A1 | 2/2005 | Chen |
| 2003/0225337 A1 | 12/2003 | Scharf et al. | | 2005/0043599 A1 | 2/2005 | O'Mara |
| 2003/0236452 A1 | 12/2003 | Melker et al. | | 2005/0043600 A1 | 2/2005 | Diab et al. |
| 2003/0236647 A1 | 12/2003 | Yoon et al. | | 2005/0049468 A1 | 3/2005 | Carlson |

| | | | | | | |
|---|---|---|---|---|---|---|
| 2005/0049470 A1 | 3/2005 | Terry | | EP | 01469773 A1 | 8/2003 |
| 2005/0049471 A1 | 3/2005 | Aceti | | EP | 1502529 | 7/2004 |
| 2005/0070773 A1 | 3/2005 | Chin | | EP | 01491135 A2 | 12/2004 |
| 2005/0075546 A1 | 4/2005 | Samsoondar | | FR | 2685865 | 1/1992 |
| 2005/0075550 A1 | 4/2005 | Lindekugel | | GB | 2 259 545 | 3/1993 |
| 2005/0085704 A1 | 4/2005 | Schulz | | JP | 63275325 A | 11/1988 |
| 2005/0090720 A1 | 4/2005 | Wu | | JP | 2013450 A | 1/1990 |
| 2005/0197548 A1 | 9/2005 | Dietiker | | JP | 2111343 A | 4/1990 |
| 2005/0228248 A1 | 10/2005 | Dietiker | | JP | 02 191434 | 7/1990 |
| 2005/0256386 A1 | 11/2005 | Chan | | JP | 2237544 A | 9/1990 |
| 2005/0272986 A1 | 12/2005 | Smith | | JP | 03 173536 | 7/1991 |
| 2005/0277819 A1 | 12/2005 | Kiani et al. | | JP | 3170866 A | 7/1991 |
| 2006/0020179 A1 | 1/2006 | Anderson | | JP | 3245042 A | 10/1991 |
| 2006/0030764 A1 | 2/2006 | Porges | | JP | 4174648 A | 6/1992 |
| 2006/0058594 A1 | 3/2006 | Ishizuka et al. | | JP | 4191642 A | 7/1992 |
| 2006/0074280 A1 | 4/2006 | Martis | | JP | 4332536 A | 11/1992 |
| 2006/0084852 A1 | 4/2006 | Mason et al. | | JP | 3124073 B | 3/1993 |
| 2006/0084878 A1 | 4/2006 | Banet | | JP | 5049624 A | 3/1993 |
| 2006/0089547 A1 | 4/2006 | Sarussi | | JP | 5049625 A | 3/1993 |
| 2006/0106294 A1 | 5/2006 | Maser et al. | | JP | 3115374 B | 4/1993 |
| 2006/0122517 A1 | 6/2006 | Banet | | JP | 2005/200031 | 8/1993 |
| 2006/0129039 A1 | 6/2006 | Lindner | | JP | 5212016 A | 8/1993 |
| 2006/0155198 A1 | 7/2006 | Schmid | | JP | 06014906 | 1/1994 |
| 2006/0173257 A1 | 8/2006 | Nagai | | JP | 6016774 B2 | 3/1994 |
| 2006/0200018 A1 | 9/2006 | Al-Ali | | JP | 3116255 B | 4/1994 |
| 2007/0032710 A1 | 2/2007 | Raridan et al. | | JP | 6029504 U | 4/1994 |
| 2007/0032712 A1 | 2/2007 | Raridan et al. | | JP | 6098881 A | 4/1994 |
| 2007/0032715 A1 | 2/2007 | Eghbal et al. | | JP | 06 154177 | 6/1994 |
| 2007/0073126 A1 | 3/2007 | Raridan, Jr. | | JP | 6269430 A | 9/1994 |
| | | | | JP | 6285048 A | 10/1994 |
| FOREIGN PATENT DOCUMENTS | | | | JP | 7001273 B2 | 1/1995 |
| DE | 3516338 | 11/1986 | | JP | 7124138 A | 5/1995 |
| DE | 37 03 458 | 8/1988 | | JP | 7136150 A | 5/1995 |
| DE | 3938759 | 5/1991 | | JP | 3116259 B | 6/1995 |
| DE | 4210102 A1 | 9/1993 | | JP | 3116260 B | 6/1995 |
| DE | 4423597 | 8/1995 | | JP | 7155311 A | 6/1995 |
| DE | 19632361 | 2/1997 | | JP | 7155313 A | 6/1995 |
| DE | 69123448 | 5/1997 | | JP | 3238813 B2 | 7/1995 |
| DE | 19703220 | 7/1997 | | JP | 7171139 A | 7/1995 |
| DE | 19640807 A1 | 9/1997 | | JP | 3134144 B | 9/1995 |
| DE | 19647877 A1 | 4/1998 | | JP | 7236625 A | 9/1995 |
| DE | 10030862 | 1/2002 | | JP | 7246191 A | 9/1995 |
| DE | 20318882 U1 | 4/2004 | | JP | 8256996 A | 10/1996 |
| EP | 0127947 | 5/1984 | | JP | 9192120 A | 7/1997 |
| EP | 00194105 B1 | 9/1986 | | JP | 10216113 A | 8/1998 |
| EP | 00204459 A3 | 12/1986 | | JP | 10216114 A | 8/1998 |
| EP | 0 262 779 | 4/1988 | | JP | 10216115 A | 8/1998 |
| EP | 0315040 | 10/1988 | | JP | 10337282 A | 12/1998 |
| EP | 0314331 | 5/1989 | | JP | 11019074 A | 1/1999 |
| EP | 00352923 A1 | 1/1990 | | JP | 11155841 A | 6/1999 |
| EP | 0 360 977 | 4/1990 | | JP | 11 188019 | 7/1999 |
| EP | 00430340 A3 | 6/1991 | | JP | 11244268 A | 9/1999 |
| EP | 0435 500 | 7/1991 | | JP | 20107157 A | 4/2000 |
| EP | 0572684 | 5/1992 | | JP | 20237170 A | 9/2000 |
| EP | 00497021 A1 | 8/1992 | | JP | 21245871 A | 9/2001 |
| EP | 0529412 | 8/1992 | | JP | 22224088 A | 8/2002 |
| EP | 0531631 | 9/1992 | | JP | 22282242 A | 10/2002 |
| EP | 0566354 | 4/1993 | | JP | 23153881 A | 5/2003 |
| EP | 0587009 | 8/1993 | | JP | 23153882 A | 5/2003 |
| EP | 00630203 B1 | 9/1993 | | JP | 23169791 A | 6/2003 |
| EP | 0 572 684 | 12/1993 | | JP | 23194714 A | 7/2003 |
| EP | 00615723 A1 | 9/1994 | | JP | 23210438 A | 7/2003 |
| EP | 00702931 A1 | 3/1996 | | JP | 23275192 A | 9/2003 |
| EP | 00724860 A1 | 8/1996 | | JP | 23339678 A | 12/2003 |
| EP | 00793942 A3 | 9/1997 | | JP | 24008572 A | 1/2004 |
| EP | 0 864 293 | 9/1998 | | JP | 24089546 A | 3/2004 |
| EP | 01006863 B1 | 10/1998 | | JP | 24113353 A | 4/2004 |
| EP | 01006864 B1 | 10/1998 | | JP | 24135854 A | 5/2004 |
| EP | 0875199 | 11/1998 | | JP | 24148069 A | 5/2004 |
| EP | 00998214 A1 | 12/1998 | | JP | 24148070 A | 5/2004 |
| EP | 0898933 | 3/1999 | | JP | 24159810 A | 6/2004 |
| EP | 01332713 A1 | 8/2003 | | JP | 24166775 A | 6/2004 |
| | | | | JP | 24194908 A | 7/2004 |

| | | |
|---|---|---|
| JP | 24202190 A | 7/2004 |
| JP | 24248819 A | 9/2004 |
| JP | 24248820 A | 9/2004 |
| JP | 24261364 A | 9/2004 |
| JP | 24290412 A | 10/2004 |
| JP | 24290544 A | 10/2004 |
| JP | 24290545 A | 10/2004 |
| JP | 24329406 A | 11/2004 |
| JP | 24329607 A | 11/2004 |
| JP | 24329928 A | 11/2004 |
| JP | 24337605 A | 12/2004 |
| JP | 24344367 A | 12/2004 |
| JP | 24351107 A | 12/2004 |
| JP | 25034472 A | 2/2005 |
| WO | WO 98/09566 A1 | 10/1989 |
| WO | WO 90/001293 A1 | 2/1990 |
| WO | WO 90/04352 | 5/1990 |
| WO | WO 91/01678 A1 | 2/1991 |
| WO | WO 91/11137 A1 | 8/1991 |
| WO | WO 92/00513 | 1/1992 |
| WO | WO 92/21281 A1 | 12/1992 |
| WO | WO 93/09711 | 5/1993 |
| WO | WO 93/13706 A2 | 7/1993 |
| WO | WO 93/16629 A1 | 9/1993 |
| WO | WO 94/03102 A1 | 2/1994 |
| WO | WO 94/23643 A1 | 10/1994 |
| WO | WO 95/02358 | 1/1995 |
| WO | WO 95/12349 A1 | 5/1995 |
| WO | WO 95/16970 | 6/1995 |
| WO | WO 96/13208 | 5/1996 |
| WO | WO 96/39927 A1 | 12/1996 |
| WO | WO 97/36536 | 10/1997 |
| WO | WO 97/36538 | 10/1997 |
| WO | WO 97/49330 A1 | 12/1997 |
| WO | WO 98/17174 A1 | 4/1998 |
| WO | WO 98/18382 | 5/1998 |
| WO | WO 98/43071 A1 | 10/1998 |
| WO | WO 98/51212 A1 | 11/1998 |
| WO | WO 98/57577 A1 | 12/1998 |
| WO | WO 99/00053 | 1/1999 |
| WO | WO 99/32030 A1 | 7/1999 |
| WO | WO 99/47039 A1 | 9/1999 |
| WO | WO 99/63884 | 12/1999 |
| WO | WO 00/21438 A1 | 4/2000 |
| WO | WO 00/28888 A1 | 5/2000 |
| WO | WO 00/59374 A1 | 10/2000 |
| WO | WO 01/13790 | 3/2001 |
| WO | WO 01/17421 A1 | 3/2001 |
| WO | WO 01/47426 | 3/2001 |
| WO | WO 0116577 | 3/2001 |
| WO | WO 01/40776 A1 | 6/2001 |
| WO | WO 01/67946 | 9/2001 |
| WO | WO 01/76461 A1 | 10/2001 |
| WO | WO 02/14793 A3 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 A1 | 1/2003 |
| WO | WO 03/001180 | 1/2003 |
| WO | WO 03/009750 A3 | 2/2003 |
| WO | WO 03/011127 A1 | 2/2003 |
| WO | WO 03/020129 | 3/2003 |
| WO | WO 03/039326 A3 | 5/2003 |
| WO | WO 03/063697 | 8/2003 |
| WO | WO 03/063697 A1 | 8/2003 |
| WO | WO 03/073924 A1 | 9/2003 |
| WO | WO 2004/000114 | 12/2003 |
| WO | WO 2004/006748 A3 | 1/2004 |
| WO | WO 2004/069046 | 8/2004 |
| WO | WO 2004/075746 A2 | 9/2004 |
| WO | WO 2005/002434 | 1/2005 |
| WO | WO 2005/009221 A2 | 2/2005 |
| WO | WO 2005/010567 A2 | 2/2005 |
| WO | WO 2005/010568 A3 | 2/2005 |
| WO | WO 2005/020120 A2 | 3/2005 |
| WO | WO 2005/065540 | 7/2005 |
| WO | WO 2006/104790 | 10/2006 |

OTHER PUBLICATIONS

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 26th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," Dissertation Book, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A. R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M. N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," Proceedings o the 26th *Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

R. Neumann, et al.; "Fourier Artifact suppression Technology Provides Reliable $SpO_2$," *Abstracts*, A11, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C. M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

\* cited by examiner

SYSTEM AND METHOD FOR PREVENTING SENSOR MISUSE

BACKGROUND OF THE INVENTION

1. Field of the Invention

The present invention relates generally to a sensor for measuring patient physiological characteristics. More particularly, embodiments of the present invention relate to a sensor that measures oxygen content in a patient's blood and that limits misuse of the sensor, such as tampering with or remanufacturing of the sensor.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Pulse oximetry may be defined as a non-invasive technique that facilitates monitoring of a patient's blood characteristics. For example, pulse oximetry may be used to measure blood oxygen saturation of hemoglobin in a patient's arterial blood and/or the patient's heart rate. Specifically, blood characteristic measurements may be acquired using a non-invasive sensor that passes light through a portion of a patient's blood perfused tissue and that photoelectrically senses the absorption and scattering of light through the blood perfused tissue. A typical signal resulting from the sensed light may be referred to as a plethysmographic waveform. Once acquired, this measurement of the absorbed and scattered light may be used with various algorithms to estimate an amount of blood constituent in the tissue, as well as other physiologic characteristics.

Conventional pulse oximeter sensors typically include emitters (e.g., a red emitter and an infrared emitter) configured to emit light waves and a photodiode detector that is arranged to detect the emitted light waves. Such sensors are typically configured to attach to a patient's finger, foot, forehead, or earlobe to facilitate measurement of blood characteristics in the associated tissue. For example, a typical oximeter sensor may be adapted to project light from the emitters through the outer tissue of a finger and into the blood vessels and capillaries inside. Such a sensor typically includes a detector that is arranged to detect the emitted light as it emerges from the outer tissue of the finger. The detector generates a signal based on the detected light and provides the signal to an oximeter, which determines blood oxygen saturation based on the signal.

Some conventional sensors also include an information element that stores information that can be read by an attached device to facilitate proper blood characteristic measurement. For example, a pulse oximeter sensor may include a memory or a resistor that can be read by an oximeter. The information stored on the information element (e.g., resistor, memory) may include parameters about the sensor. For example, the information may indicate sensor type (e.g., neonatal, pediatric, adult), the wavelengths of light produced by the emitters, and so forth. This information may be utilized in algorithms for determining values for the blood characteristic. Further, the information element may be utilized for security and quality control purposes. For example, the information element may ensure proper operation by preventing the sensor from functioning with improperly configured or unauthorized devices.

Improper remanufacturing of a sensor or tampering with the sensor can impact the quality and reliability of the sensor. For example, improper remanufacturing of a sensor may eliminate the quality assurance function of the information element or cause malfunctions by coupling incompatible sensor components together. In a specific example, an information element for a neonatal oximeter sensor may be improperly incorporated into an adult oximeter sensor during remanufacture. Such remanufacturing can cause improper operation and incorrect measurement of physiological characteristics.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present invention relate in general to a sensor for measuring patient physiological characteristics. More particularly, embodiments of the present invention relate to a sensor that measures oxygen content in a patient's blood and that includes a functional component that substantially prevents tampering with and remanufacturing of the sensor. In other words, embodiments of the present invention include a functional component that prevents efficient remanufacture of the sensor by breaking or becoming disabled when the sensor is disassembled or tampered with. For example, in one embodiment, a pulse oximeter sensor may include a conductive trace that is essential to proper operation and that breaks if the sensor is improperly disassembled. In one embodiment, the conductive trace may be required for memory operation or provide a necessary communication path for a sensor component (e.g., a light emitter or detector). In other exemplary embodiments, the sensor may include various types of functional components (e.g., memory unit, resistor) that break or stop functioning upon disassembly of the sensor, thus substantially preventing remanufacture of the sensor. For example, the sensor may include a breakable information element disposed within the sensor to facilitate measurement and ensure quality control. This information element may be arranged within the sensor to break or to become disabled upon disassembly or misuse of the sensor. For example, the information element may be a thin resistor that is coupled to multiple layers of the sensor, and when the sensor is disassembled the layers may separate causing the resistor to break.

Figure 1:
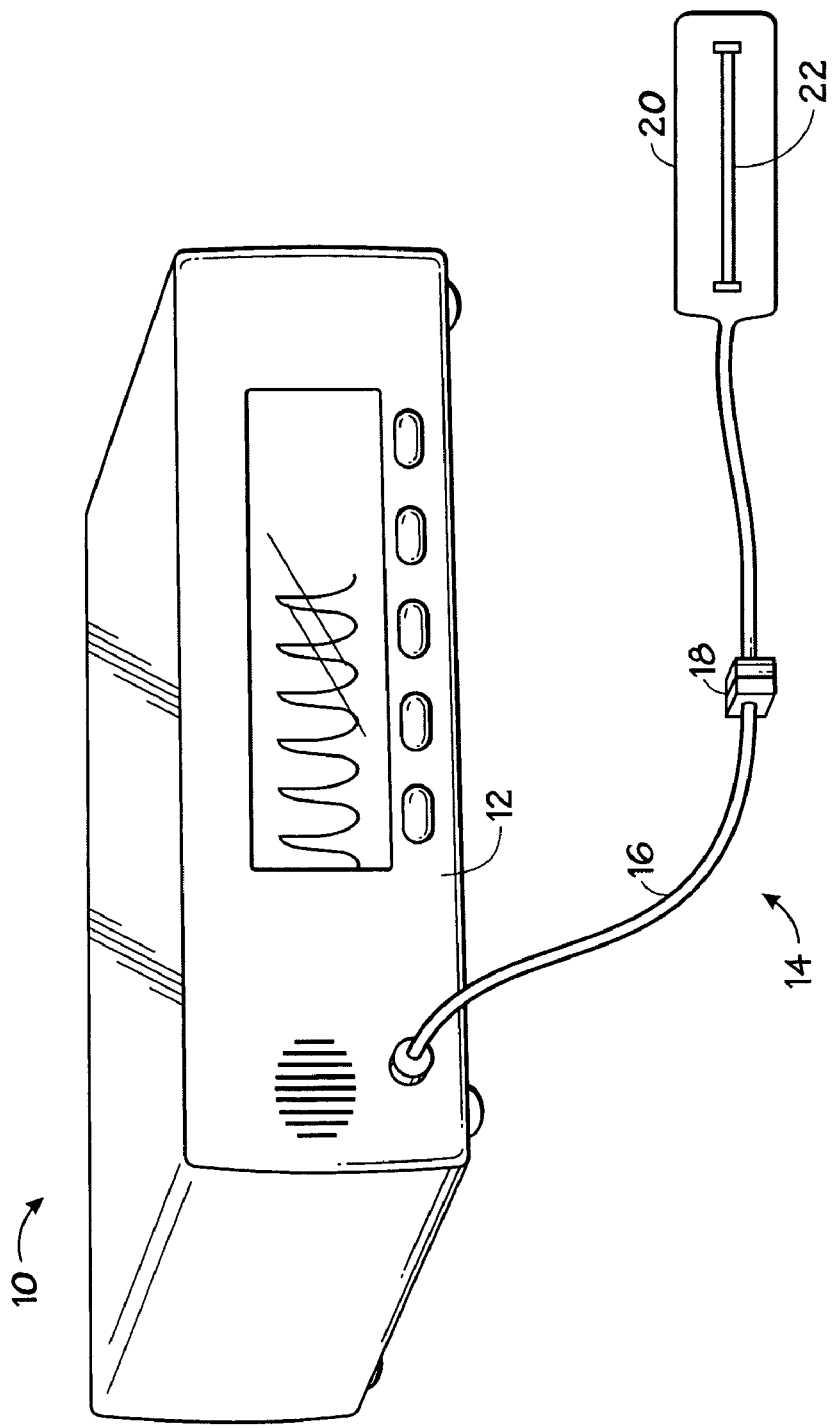
FIG. 1 is a perspective view of a patient monitor coupled to a sensor in accordance with an exemplary embodiment of the present invention.

FIG. 1 is a perspective view of a patient physiological data measurement system in accordance with an exemplary embodiment of the present invention. Specifically, FIG. 1 includes a pulse oximeter system, which is generally referred to by a reference numeral 10. The system 10 includes an oximeter 12 (e.g., computer) that communicatively couples to a sensor 14. The sensor 14 includes a sensor cable 16, a connector plug 18, and a body 20 configured to attach to a patient. The sensor 14 may be configured to couple with a patient's earlobe, finger, foot, forehead, or other locations on the patient that facilitate non-invasive measurement of desired physiological data (e.g., pulse rate, blood oxygen saturation). For example, the sensor body 20 may be configured to clip onto a patient's finger or stick on a patient's forehead. In another embodiment, the sensor 14 (e.g., an invasive brain tissue hydration sensor) may be configured for invasive operation, thus the sensor body 20 may be configured for insertion into a patient.

The sensor cable 16 and connector plug 18 may enable electronic communication from the sensor 14 to the monitor 12 and facilitate coupling and/or decoupling of the sensor 14 from the monitor 12. In some embodiments, the sensor 14 may couple directly to the monitor 12 via the sensor cable 16. In other embodiments, the sensor 14 may communicate with the monitor 12 wirelessly (e.g., via radio waves) and may not include the cable 16 or the connector plug 18. Further, it should be noted that the sensor 14 may include an internal or external quality assurance component 22 (e.g., memory, resistor, trace) that prevents operation of the sensor when disabled. The quality assurance component 22 may be arranged to break when the sensor 14 is disassembled to prevent unauthorized remanufacture of the sensor 14 and, thus, ensure that quality control is maintained. For example, the quality assurance component 22 may include conductive traces, a memory device, or a resistor with an electrical break point that will disable the sensor 14 (e.g., sever communication between sensor components) if the sensor 14 is disassembled.

Figure 2:
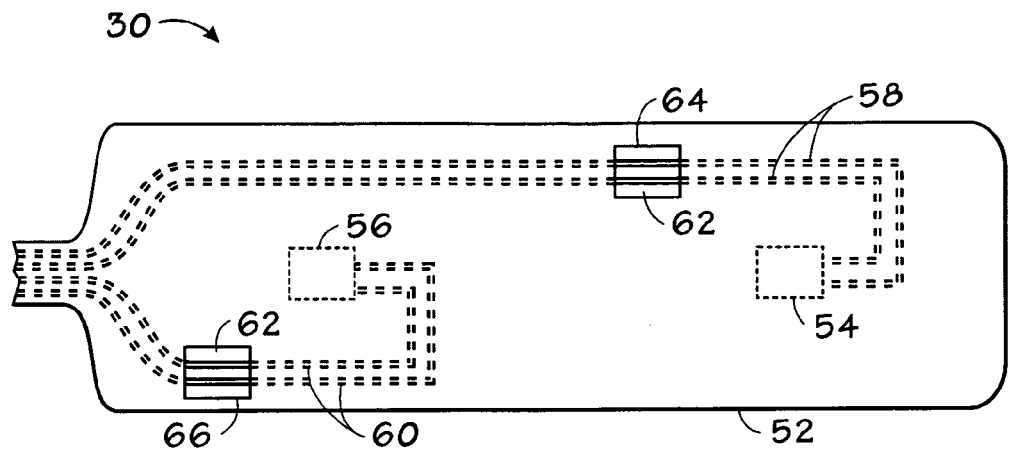
FIG. 2 is a plan view of a sensor element in accordance with an exemplary embodiment of the present invention.
Figure 3:
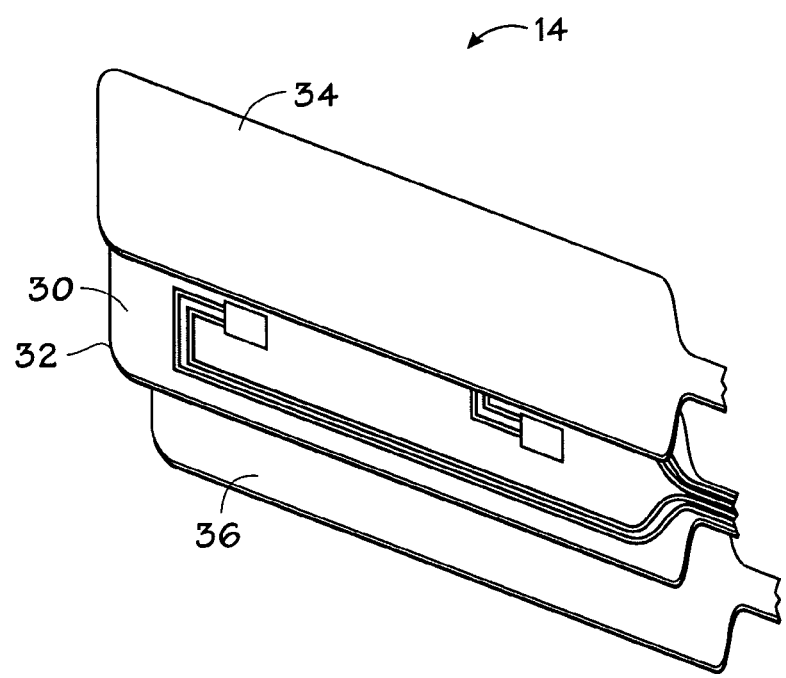
FIG. 3 is an exploded perspective view of a sensor including multiple layers in accordance with an exemplary embodiment of the present invention.

FIG. 2 is a plan view of a sensor element 30 in accordance with an exemplary embodiment of the present invention. The sensor element 30 may be a component part of the sensor 14 illustrated in FIG. 1. For example, as illustrated in the exploded view of the sensor 14 in FIG. 3, the sensor element 30 may operate as a layer of the sensor 14 that cooperates with other layers, such as a tacky connection layer 34 and a protective back covering 36, to form the sensor 14. The tacky connection layer 34 may facilitate coupling to a patient's forehead, and the protective back covering 36 may protect the sensor from damage or interference. While FIG. 3 illustrates an exploded view of the sensor 14 with the various layers separated, it should be noted that in some embodiments, the sensor 14 may be assembled such that the layers (e.g., layers 32, 34, and 36) are substantially inseparable without damaging sensor components (e.g., quality assurance component 22) that are essential to sensor operation. For example, in one embodiment, the layers may be interwoven with the quality assurance component 22 (e.g., a thin wire) to prevent separation of the layers without breaking the quality assurance component 22.

Figure 4:
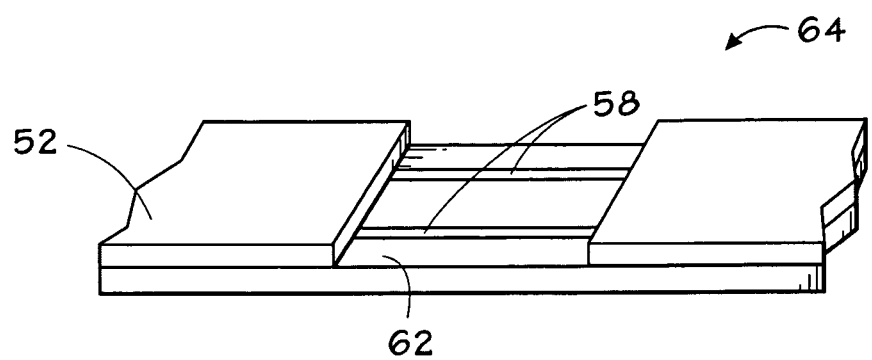
FIG. 4 is a magnified perspective view of exposed traces on a sensor element in accordance with an exemplary embodiment of the present invention.

The sensor element 30 may correspond in shape to the body 20 of the sensor 14. In the illustrated embodiment, the sensor element 30 is elongate and flexible to facilitate conformation of the sensor 14 to a patient's forehead or to facilitate wrapping the sensor 14 about the patient's finger. Further, in the illustrated embodiment of FIG. 4, the sensor element 30 includes an insulation layer 52, an emitter component 54, and a detector component 56. The emitter component 54 is coupled with a first pair of conductive traces 58. The first pair of conductive traces facilitates communication with an external device (e.g., oximeter 12). Similarly, the detector component 56 is coupled with a second pair of conductive traces 60 that facilitate communication with the external device. It should be noted that in some embodiments, the sensor 14 may be formed from a hard or rigid material (e.g., hard plastic).

Figure 5:
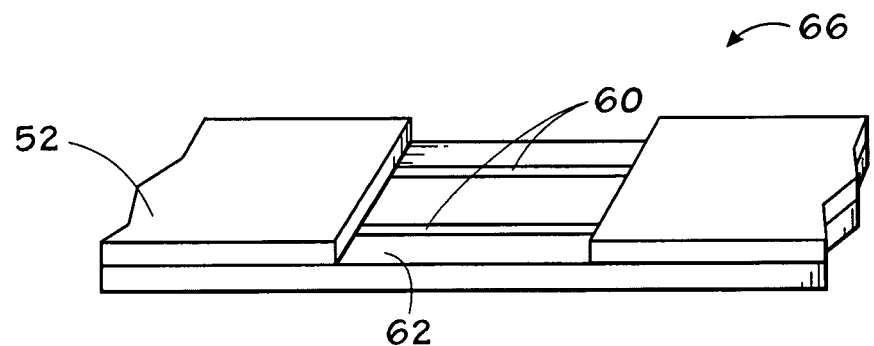
FIG. 5 is a magnified perspective view of exposed traces on a sensor element in accordance with an exemplary embodiment of the present invention.

As illustrated in FIG. 2, a majority of the components of the sensor element 30 are covered by the insulation layer 52. Indeed, the dashed lines indicate that the emitter component 54, the detector component 56, and a substantial portion of the conductive traces 58 and 60 are protectively covered by the insulation layer 52. However, certain portions of the conductive traces 58 and 60 are not covered by the insulation layer 52 and are exposed in their location on a base layer 62. These exposed areas are indicated by reference numerals 64 and 66, respectively. A magnified perspective view of the exposed area 64 is provided in FIG. 4, and a magnified perspective view of the exposed area 66 is provided in FIG. 5. By not covering the areas 64 and 66, the operability of the conductive traces 58 and 60, along with the functionality of the entire sensor 14 may be made vulnerable to tampering with or disassembly of the sensor 14. Indeed, the exposed portions of the traces 58 and 60 may be coupled to a separate component of the sensor that will break the traces 58 and 60 if removed from the sensor element 30.

Figure 6:
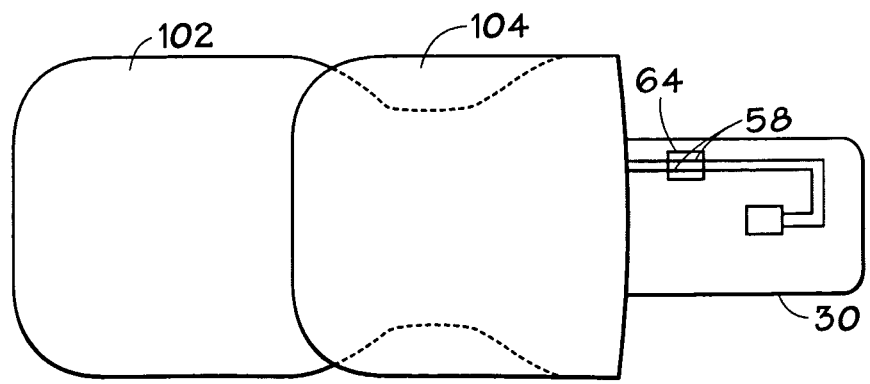
FIG. 6 is a plan view of a sensor with a bandage layer of the sensor partially peeled away from a sensor element in accordance with an exemplary embodiment of the present invention.

As set forth above, the exposed areas 64 and 66 facilitate disablement of the sensor element 30 upon disassembly of the sensor 14. For example, as illustrated in FIG. 6, a bandage 102 may be coupled to the sensor element 30 to form the sensor 14 and to facilitate coupling of the sensor 14 to a patient. Indeed, the bandage 102 may include a tacky substance 104 on one side that is adapted to stick to a patient's skin. The bandage 102 may also couple directly to the conductive traces 58 and 60 at the exposed areas 64 and 66 (e.g., via the tacky substance 104). When the bandage 102 becomes worn (e.g., the tacky substance 104 is substantially absent on portions of the bandage 102 that couple to the patient), an unauthorized manufacturer may wish to remanufacture the sensor 14 by removing the sensor element 30 and coupling it with a different bandage or other coupling device. It should be noted that other similar situations may also arise that encourage disassembly of the sensor 14 and reuse of the sensor element 30 or other sensor components in an unauthorized and inappropriate manner.

Figure 7:
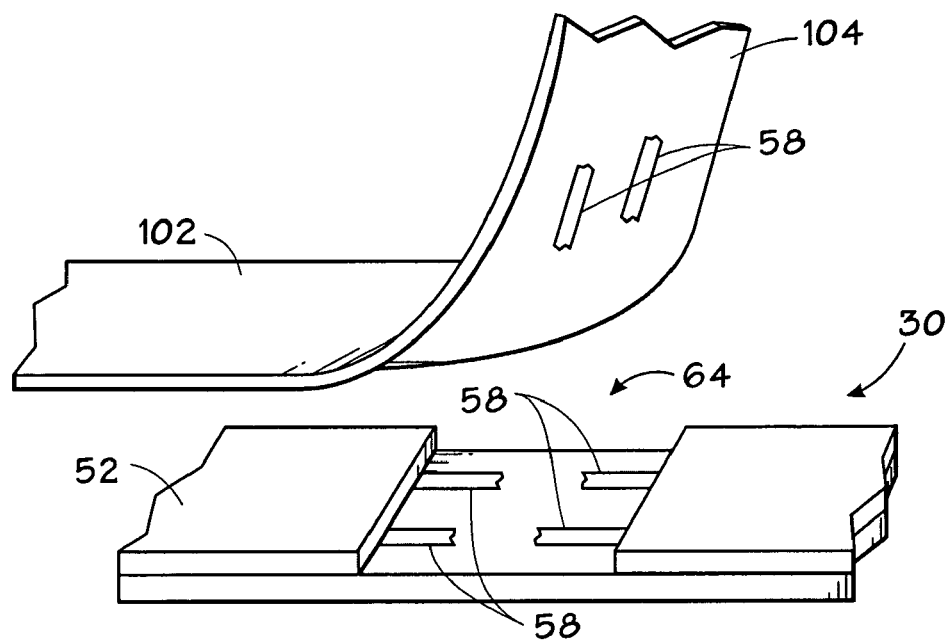
FIG. 7 is a magnified perspective view of a disassembled sensor with torn traces on separate disassembled layers of the sensor in accordance with an exemplary embodiment of the present invention.
Figure 8:
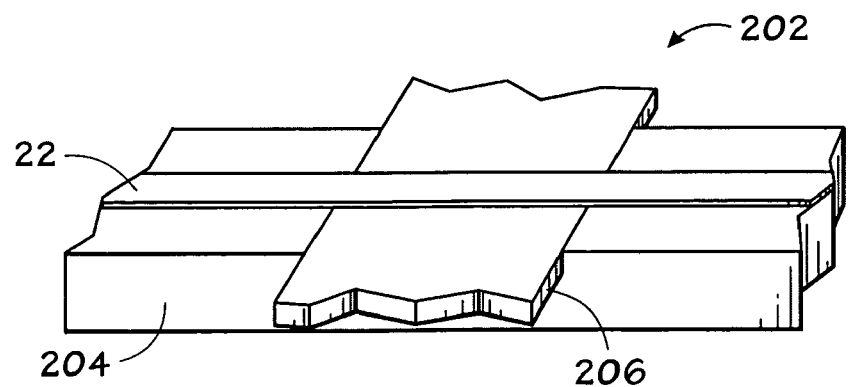
FIG. 8 is a magnified perspective view of a quality assurance component disposed over an intersection of a first sensor layer and a second sensor layer in accordance with an exemplary embodiment of the present invention.

As set forth above, in accordance with present embodiments, disassembly of the sensor 14 (e.g., removal of the bandage 102 from the sensor element 30), tampering with the sensor 14, and other types of misuse may result in disabling the sensor 14 (e.g., tearing the conductive traces 58 and 60). For example, FIG. 7 is a magnified view of the exposed area 64 after the bandage 102 has been removed from a coupling with the sensor element 30. In the illustrated embodiment, portions of the conductive traces 58 at the exposed area 64 remain coupled to the bandage 102 when it is removed, thus tearing the traces 58, disabling the entire sensor element 30, and substantially preventing remanufacture. While traces 58 and 60 are used in the illustrated embodiment, in other embodiments various breakable quality assurance components (e.g., memory, resistor) may be utilized. Further, in some embodiments, the quality assurance component 22 may be disposed over an intersection 202 of a first sensor layer 204 and a second sensor layer 206, as illustrated in FIG. 8. By placing the quality assurance component 22 over the intersection 202 (or electrical breakpoint), severance of the quality assurance component 22 is essentially assured by separation of the two layers 204 and 206.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A pulse oximetry sensor, comprising:
an emitter configured to transmit a signal into tissue;
a detector configured to detect the signal; and
a quality assurance component coupled to a first sensor component and second sensor component, the quality assurance component configured to break and disable the sensor upon separation of the first sensor component from the second sensor component, wherein the quality assurance component is interwoven with the first sensor component and the second sensor component.

2. The sensor of claim 1, wherein the quality assurance component comprises a trace.

3. The sensor of claim 1, wherein the quality assurance component comprises an information element.

4. The sensor of claim 1, wherein the quality assurance component comprises a memory.

5. The sensor of claim 1, wherein the quality assurance component comprises a resistor.

6. The sensor of claim 1, wherein the quality assurance component comprises a communication component configured to provide electrical communication with a monitor.

7. The sensor of claim 1, wherein the first and second sensor components are first and second sensor layers and the quality assurance component is disposed across the first and second layers.

8. The sensor of claim 1, wherein a portion of the quality assurance component couples to the second sensor component at an exposed location on the first sensor component, the exposed location defining an electrical breakpoint.

9. The sensor of claim 1, wherein the first and second sensor components are first and second sensor layers and the quality assurance component is interwoven with the first and second layers.

10. A method of assured quality operation of a pulse oximetry sensor, comprising:
disabling the pulse oximetry sensor upon separation of a first sensor component and a second sensor component by breaking a quality assurance component that is interwoven with the first and second sensor components.

11. The method of claim 10, wherein breaking the quality assurance component comprises breaking a conductive trace to disable the pulse oximetry sensor.

12. The method of claim 10, wherein breaking the quality assurance component comprises breaking an information element to disable the pulse oximetry sensor.

13. The method of claim 10, wherein breaking the quality assurance component comprises breaking a memory to disable the pulse oximetry sensor.

14. The method of claim 10, wherein breaking the quality assurance component comprises breaking a resistor to disable the pulse oximetry sensor.

15. The method of claim 10, comprising breaking the quality assurance component proximate an electrical break point.

16. The method of claim 15, wherein breaking the quality assurance component proximate the electrical break point comprises breaking the quality assurance component proximate a junction between the first and second sensor components.

17. A method of manufacturing a quality assured pulse oximetry sensor, comprising:
providing an emitter configured to transmit a signal into tissue;
providing a detector configured to detect the signal; and
providing a quality assurance component interwoven with a first sensor component and second sensor component, the quality assurance component configured to break and disable the sensor upon separation of the first sensor component from the second sensor component.

18. The method of claim 17, wherein the quality assurance component comprises a trace.

19. The method of claim 17, wherein the quality assurance component comprises an information element.

20. The method of claim 17, comprising disposing the quality assurance component across a junction between the first and second sensor components.

21. The method of claim 17, comprising coupling a portion of the quality assurance component to the second sensor component at an exposed location on the first sensor component, the exposed location defining an electrical breakpoint.

* * * * *